(12) United States Patent
Dekel et al.

(10) Patent No.: US 10,952,864 B2
(45) Date of Patent: Mar. 23, 2021

(54) GLENOID COMPONENT FOR SHOULDER ARTHROPLASTY

(71) Applicant: Stryker European Operations Limited, Carrigtwohill (IE)

(72) Inventors: Assaf Dekel, Or Yehuda (IL); Idan Tobis, Caesarea (IL); Ruth Icekson, Caesarea (IL)

(73) Assignee: Stryker European Operations Limited

( * ) Notice: Subject to any disclaimer, the term of this patent is extended or adjusted under 35 U.S.C. 154(b) by 0 days.

(21) Appl. No.: 16/977,312

(22) PCT Filed: Jan. 28, 2019

(86) PCT No.: PCT/IB2019/050687
§ 371 (c)(1),
(2) Date: Sep. 1, 2020

(87) PCT Pub. No.: WO2019/166887
PCT Pub. Date: Sep. 6, 2019

(65) Prior Publication Data
US 2021/0000606 A1    Jan. 7, 2021

Related U.S. Application Data

(60) Provisional application No. 62/637,217, filed on Mar. 1, 2018.

(51) Int. Cl.
*A61F 2/40*         (2006.01)

(52) U.S. Cl.
CPC .................. *A61F 2/4081* (2013.01)

(58) Field of Classification Search
CPC .. A61F 2/4081; A61F 2/40; A61F 2/34; A61F 2002/3443; A61F 2002/4022
See application file for complete search history.

(56) References Cited

U.S. PATENT DOCUMENTS

| 6,364,910 B1 | 4/2002 | Shultz et al. |
| 2006/0155383 A1 | 7/2006 | Smith et al. |
| 2007/0100458 A1 | 5/2007 | Dalla Pria |

OTHER PUBLICATIONS

International Search Report including Written Opinion for Application No. PCT/IB19/50687, dated Aug. 9, 2019, pp. 1-9.

*Primary Examiner* — Dinah Baria
(74) *Attorney, Agent, or Firm* — Lerner, David, Littenberg, Krumholz & Mentlik, LLP (57) ABSTRACT

An apparatus including a prosthetic glenoid component for use in shoulder arthroplasty for articulation with a humeral head. The prosthetic glenoid component includes a bearing body, which is shaped so as to define (a) a concave bearing surface for articulation with the humeral head, and (b) a convex glenoid-contacting surface; and one or more superior cantilevers, which (a) jut out from a periphery of the bearing body, (b) are more flexible than the bearing body, and (c) resist, without preventing, superior migration of the humeral head. In shoulder arthroplasty, providing a prosthetic glenoid component for articulation with a humeral head, and implanting the prosthetic glenoid component such that the convex glenoid-contacting surface contacts a glenoid cavity, and the one or more superior cantilevers resist, without preventing, superior migration of the humeral head.

19 Claims, 6 Drawing Sheets

GLENOID COMPONENT FOR SHOULDER ARTHROPLASTY

CROSS-REFERENCE TO RELATED APPLICATIONS

The present application is a national phase entry under 35 U.S.C. § 371 of International Application No. PCT/IB2019/050687, filed Jan. 28, 2019, published in English as WO 2019/166887 A1, which claims priority from U.S. Provisional Application No. 62/637,217 filed on Mar. 1, 2018, all of which are incorporated by reference herein in their entirety.

TECHNICAL FIELD

The present invention relates generally to surgical implants, and specifically to prosthetic glenoid components for shoulder arthroplasty.

BACKGROUND

In shoulder replacement surgery, the damaged parts of the shoulder are removed and replaced with prostheses. Generally, either the head of the humerus is replaced or resurfaced, or both the head of the humerus and the glenoid are replaced (total shoulder arthroplasty).

SUMMARY

Embodiments of the present invention provide a prosthetic glenoid component for use in shoulder arthroplasty for articulation with a humeral head. The prosthetic glenoid component may be most appropriate for patients with damaged muscles (particularly the supraspinatus and/or infraspinatus muscles) and/or tendons of the rotator cuff that ordinarily prevent superior migration of (i.e., hold down) the humeral head.

The prosthetic glenoid component includes:
  a bearing body, which is shaped so as to define (a) a concave bearing surface for articulation with the humeral head, and (b) a convex glenoid-contacting surface; and
  one or more (e.g., two or more) superior cantilevers, which (a) jut out from a periphery of the bearing body, (b) are more flexible than the bearing body, and (c) resist, without preventing, superior migration of the humeral head.

For applications in which the prosthetic glenoid component includes two or more superior cantilevers, the superior cantilevers are shaped and arranged so as to be able to flex independently of one another, thereby generally mimicking the natural muscles and/or tendons of the rotator cuff, re-balancing the shoulder and preserving the center of rotation.

For some applications, the bearing body is shaped so as to define one or more inferior hooks, which extend from the convex glenoid-contacting surface around a hooked peripheral portion of the periphery of the bearing body. The one or more inferior hooks apply a counterforce against a glenoid cavity to offset the moment of force resulting from the superiorly-directed force applied by the superior cantilevers.

One application provides an apparatus including a prosthetic glenoid component for use in shoulder arthroplasty for articulation with a humeral head, the prosthetic glenoid component including:
  a bearing body, which is shaped so as to define (a) a concave bearing surface for articulation with the humeral head, and (b) a convex glenoid-contacting surface; and
  one or more superior cantilevers, which (a) jut out from a periphery of the bearing body, (b) are more flexible than the bearing body, and (c) resist, without preventing, superior migration of the humeral head.

For some applications, the one or more superior cantilevers define respective convex anterior surfaces. Alternatively, for some applications, the one or more superior cantilevers define respective flat anterior surfaces.

For some applications, the one or more superior cantilevers have an average width of between 1 and 8 mm.

For some applications, respective ends of the one or more superior cantilevers farthest from the periphery of the bearing body are rounded.

For some applications, the one or more superior cantilevers define respective anterior surfaces having an aggregate area of between 200 and 1200 $mm^2$. Alternatively or additionally, for some applications, the one or more superior cantilevers define respective anterior surfaces having an aggregate area of between 20% and 100% of an area of the concave bearing surface of the bearing body.

For some applications, for each of the one or more superior cantilevers, a length thereof is between 10 and 40 mm, measured along an anterior surface of the superior cantilever between (a) a first point on the superior cantilever farthest from the periphery of the bearing body and (b) a second point on the periphery of the bearing body closest to the first point.

For some applications, each of the one or more superior cantilevers has an average width equal to between 10% and 90% of the length thereof. Alternatively or additionally, for some applications, each of the one or more superior cantilevers has an average thickness of between 100 and 1000 microns.

For some applications:
  the periphery of the bearing body defines a best-fit plane, and
  for each of the one or more superior cantilevers:
    a line is defined by (a) a first point on the superior cantilever farthest from the periphery of the bearing body and (b) a second point on the periphery of the bearing body closest to the first point, and
    the line forms an angle of between 15 and 90 degrees with the best-fit plane.

For some applications, the angle is between 30 and 60 degrees.

For some applications, the periphery of the bearing body includes one or more smoothly curved portions.

For some applications, the one or more superior cantilevers include elastic nitinol.

For some applications, the concave bearing surface has a hardness of between 55 and 80 Shore D.

For some applications, each of the one or more superior cantilevers has a base that extends along between 10% and 30% of a length of the periphery of the bearing body. Alternatively or additionally, for some applications, each of the one or more superior cantilevers has a base that extends along between 1 and 10 mm of the periphery of the bearing body.

For some applications, the one or more superior cantilevers have respective bases that in aggregate extend along between 1 and 10 mm of the periphery of the bearing body.

For some applications:

the one or more superior cantilevers have respective bases, all of which are connected to a cantilevered peripheral portion of the periphery of the bearing body, and the cantilevered peripheral portion is delineated by the rays of an angle, which has its vertex at the centroid of the periphery of the bearing body, and is no more than 45 degrees.

For some applications, respective ends of the one or more superior cantilevers farthest from the periphery of the bearing body are configured to deflect between 1 and 5 mm upon application of a superiorly-directed force of 1 kN on the one or more superior cantilevers.

For any of the applications described above, the prosthetic glenoid component may include two or more superior cantilevers, such as three or more superior cantilevers, or four or more superior cantilevers. For some applications, the two or more superior cantilevers are shaped and arranged so as to be able to flex independently of one another. For some applications, the two or more superior cantilevers, when unconstrained, are shaped so as define respective gaps between adjacent ones of the two or more superior cantilevers. For some applications, each of the gaps has average width of between 0.1 and 2 mm. Alternatively or additionally, for some applications, each of the gaps has average width of between 2.5% and 100% of an average width of the two or more superior cantilevers. For some applications, the two or more superior cantilevers are connected to one another only within 4 mm of the periphery of the bearing body. For some applications, the two or more superior cantilevers are connected to one another only via the bearing body. For some applications, the two or more superior cantilevers are connected to one another by one or more flexible connecting members. For some applications, the two or more superior cantilevers have respective bases that in aggregate extend along between 30% and 50% of a length of the periphery of the bearing body. For some applications, the two or more superior cantilevers have identical shapes, while for other applications, the two or more superior cantilevers have different shapes from one another.

For any of the described applications, the bearing body may be shaped so as to define one or more inferior hooks, which extend from the convex glenoid-contacting surface around a hooked peripheral portion of the periphery of the bearing body. For some applications, the one or more superior cantilevers have respective bases, all of which are connected to a cantilevered peripheral portion of the periphery of the bearing body, and the hooked peripheral portion is disposed on the periphery opposite the cantilevered peripheral portion. For some applications, the one or more hooks have an average height from the convex glenoid-contacting surface of between 2 and 20 mm.

There is further provided, in accordance with an embodiment of the present invention, a method including:

providing a prosthetic glenoid component for use in shoulder arthroplasty for articulation with a humeral head, the prosthetic glenoid component including (a) a bearing body, which is shaped so as to define (i) a concave bearing surface for articulation with the humeral head, and (ii) a convex glenoid-contacting surface, and (b) one or more superior cantilevers, which (i) jut out from a periphery of the bearing body, and (ii) are more flexible than the bearing body; and as part of the shoulder arthroplasty, implanting the prosthetic glenoid such that the convex glenoid-contacting surface contacts a glenoid cavity, and the one or more superior cantilevers resist, without preventing, superior migration of the humeral head.

Embodiments of the present invention will be more fully understood from the following detailed description of embodiments thereof, taken together with the drawings, in which:

DETAILED DESCRIPTION

FIGS. 1A-E are schematic illustrations of a prosthetic glenoid component 10 for use in shoulder arthroplasty. Prosthetic glenoid component 10 is configured to articulate with a humeral head 12 (shown in FIG. 5B), which may be (a) prosthetic (in a total shoulder arthroplasty), (b) bony (natural) (in a glenoid-only shoulder arthroplasty), or (c) resurfaced (e.g., either all or part of the humeral head bone has been replaced with a smooth metal ball). Prosthetic glenoid component 10 is typically implanted as part of a total shoulder joint replacement procedure (in which a prosthetic humeral head is additionally implanted) or a glenoid-only shoulder joint replacement procedure in which prosthetic glenoid component 10 is implanted and the natural humeral head is left in place). Prosthetic glenoid component 10 may be most appropriate for patients with damaged muscles (particularly the supraspinatus and/or infraspinatus muscles) and/or tendons of the rotator cuff that ordinarily prevent superior migration of (i.e., hold down) humeral head 12.

Prosthetic glenoid component 10 includes:

a bearing body 20, which is shaped so as to define (a) a concave bearing surface 22 for articulation with humeral head 12, and (b) a convex glenoid-contacting surface 24 (concave bearing surface 22 and convex glenoid-contacting surface 24 face in generally opposite directions); and one or more (e.g., two or more) superior cantilevers 26, which (a) jut out from a periphery 28 of bearing body 20, (b) are more flexible than bearing body 20, and (c) resist, without preventing, superior migration of humeral head 12.

The one or more (e.g., two or more) superior cantilevers 26 are typically springy, elongate projecting flexible beams fixed to bearing body 20 at one end of each of the superior cantilevers. The one or more (e.g., two or more) superior cantilevers 26 may be generally shaped as fingers.

The one or more (e.g., two or more) superior cantilevers 26 define respective anterior surfaces 30. For some applications, anterior surfaces 30 are convex, such as shown in the figures, while for other applications, anterior surfaces 30 are flat (configuration not shown). For some applications, the respective anterior surfaces 30 have an aggregate area of (a) at least 200 mm², no more than 1200 mm², and/or between 200 and 1200 mm², such as at least 400 mm², no more than 1000 mm², and/or between 400 and 1000 mm², and/or (b) at least 20%, no more than 100%, and/or between 20% and 100% of an area of concave bearing surface 22 of bearing body 20, such as at least 30%, no more than 90%, and/or between 30% and 90% of the area.

Figure 1A:
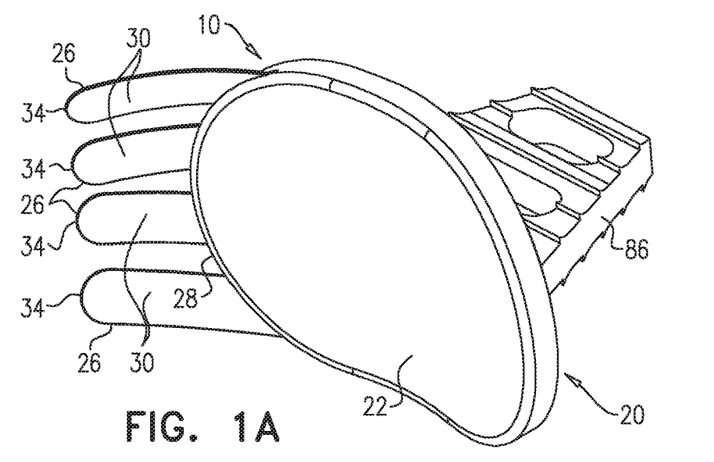
FIGS. 1A-E are schematic illustrations of a prosthetic glenoid component for use in shoulder arthroplasty.

Reference is made to FIG. 1A. For some applications, respective ends 34 of the one or more (e.g., two or more) superior cantilevers 26 farthest from periphery 28 of bearing body 20 are rounded (optionally, but not necessarily, circular), as shown in the figures. For some applications, respective ends 34 of the one or more (e.g., two or more) superior cantilevers 26 farthest from periphery 28 of bearing body 20 are configured to deflect between 1 and 5 mm upon application of a superiorly-directed force of 1 kN on the one or more (e.g., two or more) superior cantilevers (the force is applied by humeral head 12).

Figures 1B, 1C:
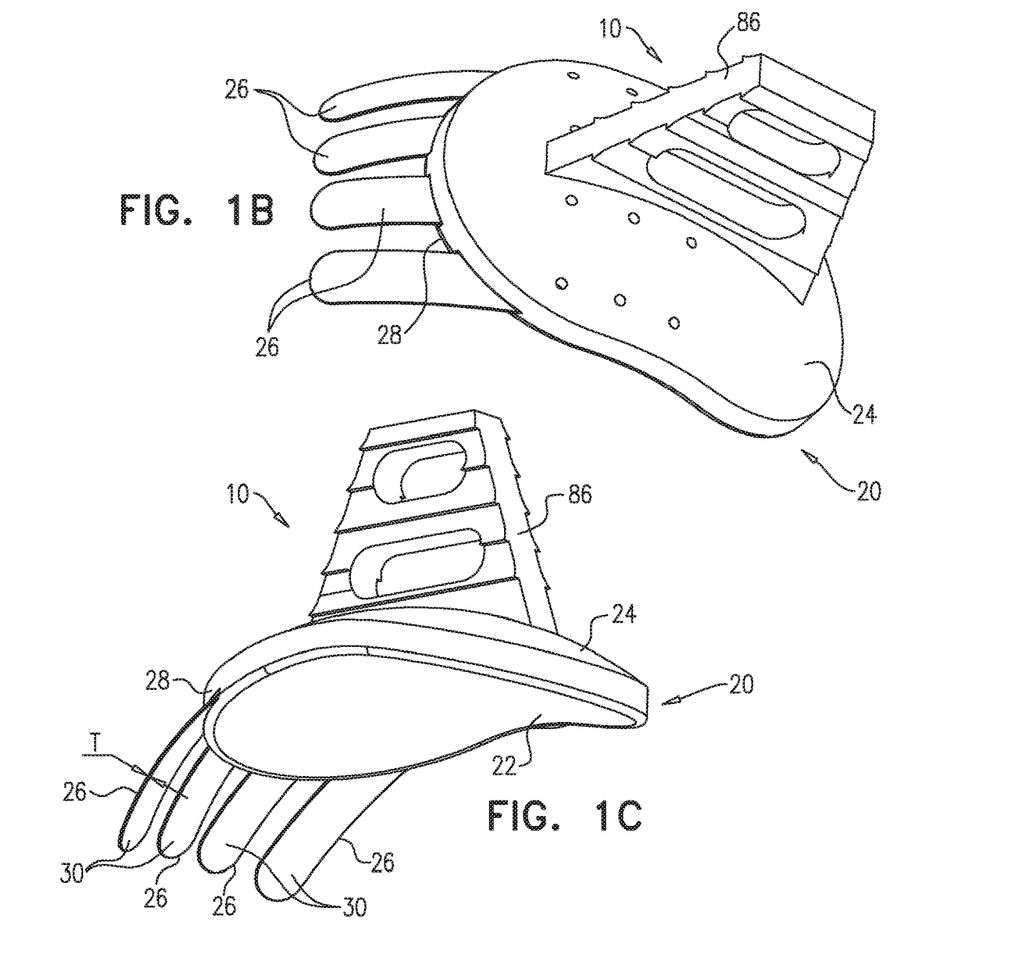

Reference is made to FIG. 1C. For some applications, each of the one or more (e.g., two or more) superior cantilevers 26 has an average thickness T of at least 100 microns (e.g., at least 200 microns), no more than 4000 microns (e.g., no more than 2000 microns), and/or between 100 and 4000 microns, e.g., between 200 and 2000 microns.

Figure 1D:
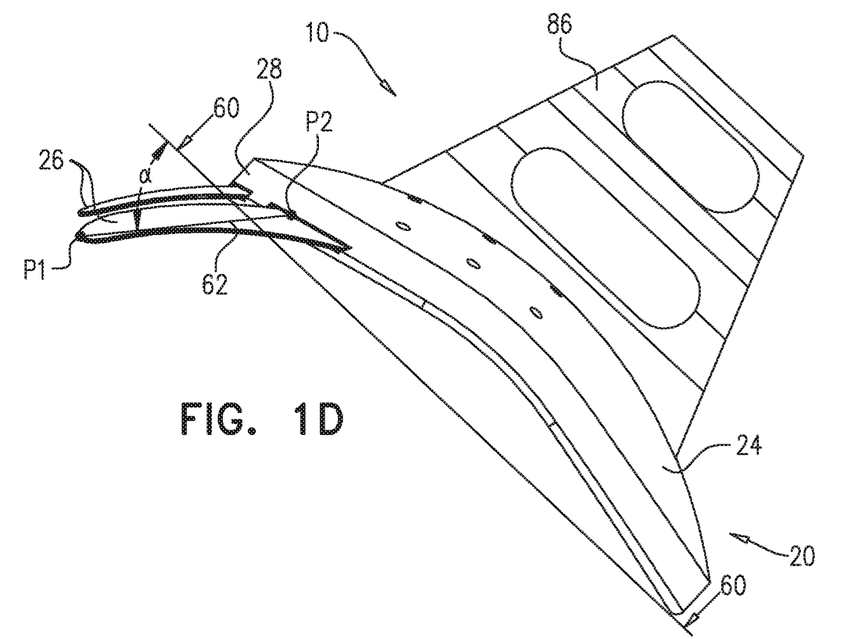

Reference is made to FIG. 1D. Periphery 28 of bearing body 20 defines a best-fit plane 60 (plane 60 is flat, and is derived using the least square orthogonal distances between the points around the cusp of periphery 28). For each of the one or more (e.g., two or more) superior cantilevers 26, a line 62 is defined by (a) first point P1 on superior cantilever 26 farthest from periphery 28 of bearing body 20 (b) second point P2 on periphery 28 of bearing body 20 closest to first point P1. For some applications, for each of the one or more (e.g., two or more) superior cantilevers 26, line 62 forms an angle α (alpha) of between 15 and 90 degrees with best-fit plane 60, such as between 20 and 60 degrees, e.g., between 30 and 45 degrees. As used in the present application, including in the claims, an angle between a line and a plane is the smaller of the two supplementary angles between the line and the plane, or equals 90 degrees if the line and the plane are perpendicular.

Figure 1E:
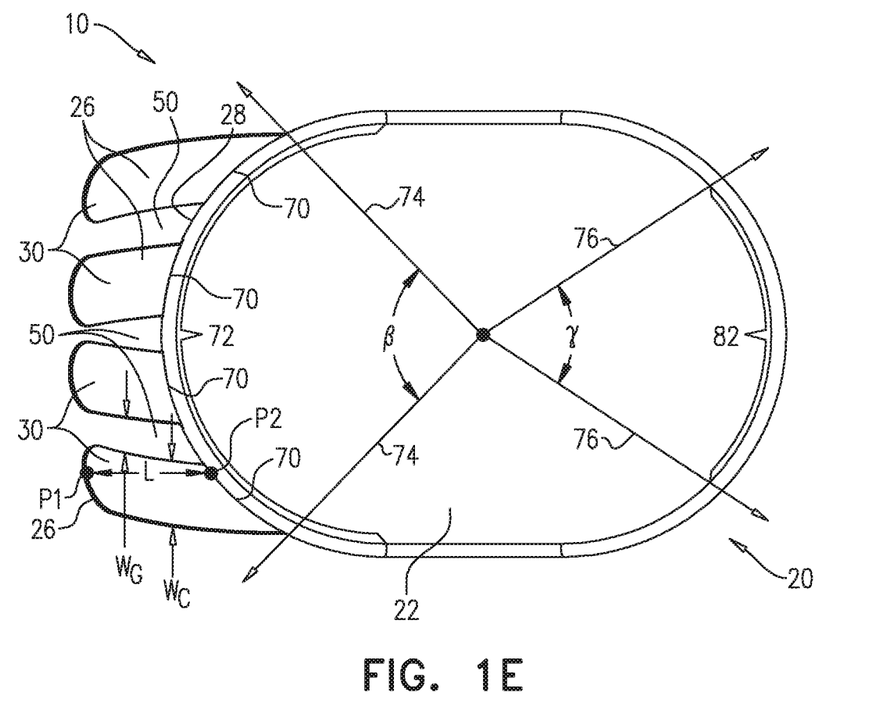

Reference is made to FIG. 1E. For some applications, the one or more (e.g., two or more) superior cantilevers 26 have an average width $W_C$ of at least 1 mm (e.g., at least 2 mm), no more than 40 mm (e.g., no more than 8 mm), and/or between 1 and 40 mm, e.g., between 2 and 8 mm. (Each of the superior cantilevers 26 has an average width, and the average width $W_C$ of two or more superior cantilevers 26 equals the average of these average widths. The average width $W_C$ of one of superior cantilevers 26 is labeled in FIG. 1E.)

Reference is still made to FIG. 1E. For some applications, for each of the one or more (e.g., two or more) superior cantilevers 26, a length L thereof is at least 10 mm (e.g., at least 20 mm), no more than 60 mm (e.g., no more than 40 mm), and/or between 10 and 60 mm, e.g., between 20 and 40 mm, measured along anterior surface 30 of superior cantilever 26 (i.e., on anterior surface 30, rather than as the crow flies) between (a) first point P1 on superior cantilever 26 farthest from periphery 28 of bearing body 20 and (b) second point P2 on periphery 28 of bearing body 20 closest to first point P1. For some applications, the average width $W_C$ of each of the one or more (e.g., two or more) superior cantilevers 26 equals at least 10% (e.g., at least 20%), no more than 90% (e.g., no more than 70%), and/or between 10% and 90% of the length L thereof, e.g., between 20% and 70% of the length L thereof.

Reference is still made to FIG. 1E. For some applications, each of the one or more (e.g., two or more) superior cantilevers 26 has a base 70 that extends along (a) between 10% and 30% of a length of periphery 28 of bearing body 20 (the length is measured around the periphery), and/or (b) at least 1 mm (e.g., at least 5 mm), no more than 40 mm (e.g., no more than 20 mm), and/or between 1 and 40 mm, e.g., between 5 and 20 mm, of periphery 28 of bearing body 20. For some applications in which prosthetic glenoid component 10 includes two or more superior cantilevers 26, the two or more superior cantilevers 26 have respective bases 70 that in aggregate extend along (a) at least 20% (e.g., at least 30%), no more than 60% (e.g., no more than 50%), and/or between 30% and 50%, e.g., between 20% and 50%, of the length of periphery 28 of bearing body 20, and/or (b) at least 1 mm (e.g., at least 5 mm), no more than 40 mm (e.g., no more than 8 mm), and/or between 1 and 40 mm, e.g., between 5 and 8 mm, of periphery 28 of bearing body 20.

Reference is still made to FIG. 1E. For some applications, the one or more (e.g., two or more) superior cantilevers 26 have respective bases 70, all of which are connected to a cantilevered peripheral portion of periphery 28 of bearing body 20. Cantilevered peripheral portion 72 is delineated by rays 74 of an angle β (beta), which has its vertex 76 at the centroid of periphery 28 of bearing body 20, and is at least 15 degrees, no more than 60 degrees, and/or between 15 and 60 degrees.

Reference is again made to FIGS. 1A-E. For some applications, the one or more (e.g., two or more) superior cantilevers 26 include superelastic nitinol. For some applications, concave bearing surface 22 has a hardness of at least 55 Shore D (e.g., at least 70 Shore D), no more than 85 Shore D (e.g., no more than 80 Shore D), and/or between 55 and 85 Shore D (e.g., between 70 and 80 Shore D), i.e., is generally rigid. For example, concave bearing surface 22 may include titanium, cobalt, or a polymer, and may be machined or molded from UHMWPE, PEEK, PEKK, PTFE, or similar tough and smooth polymers.

Reference is still made to FIGS. 1A-E. For some applications, as shown in the figures, prosthetic glenoid component 10 includes two or more superior cantilevers 26, such as three or more superior cantilevers 26, e.g., four or more superior cantilevers 26. For some of these applications, the two or more superior cantilevers 26 have identical shapes, while for other applications, the two or more superior cantilevers 26 have different shapes from one another. Alternatively, prosthetic glenoid component 10 includes exactly one superior cantilever 26 (configuration not shown).

Typically, the two or more superior cantilevers 26 are shaped and arranged so as to be able to flex independently of one another, thereby generally mimicking the natural muscles and/or tendons of the rotator cuff, re-balancing the shoulder and preserving the center of rotation. Typically, the two or more superior cantilevers 26, when unconstrained, are shaped so as define respective gaps 50 between adjacent ones of the two or more superior cantilevers 26 (labeled in FIG. 1E). For some applications, each of gaps 50 has average width $W_G$ of at least 0.1 mm, no more than 2 mm, and/or between 0.1 and 2 mm, such as at least 0.2 mm, no more than 1.5 mm, and/or between 0.2 and 1.5 mm, and/or at least 2.5%, no more than 100% (e.g., no more than 75% or no more than 50%), and/or between 2.5% and 100% (e.g., 75% or 50%) of the average width $W_C$ of the two or more superior cantilevers 26, such as at least 1%, no more than 10%, and/or between 1% and 10% of the average width $W_C$ (labeled in FIG. 1E).

Figure 2A:
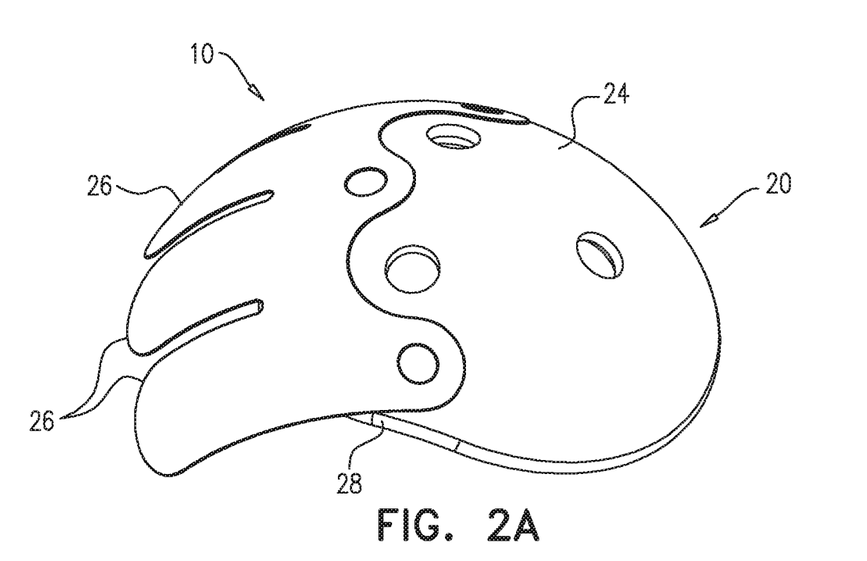
FIGS. 2A-B are schematic illustrations of another configuration of the prosthetic glenoid component of FIGS. 1A-E.
Figure 2B:
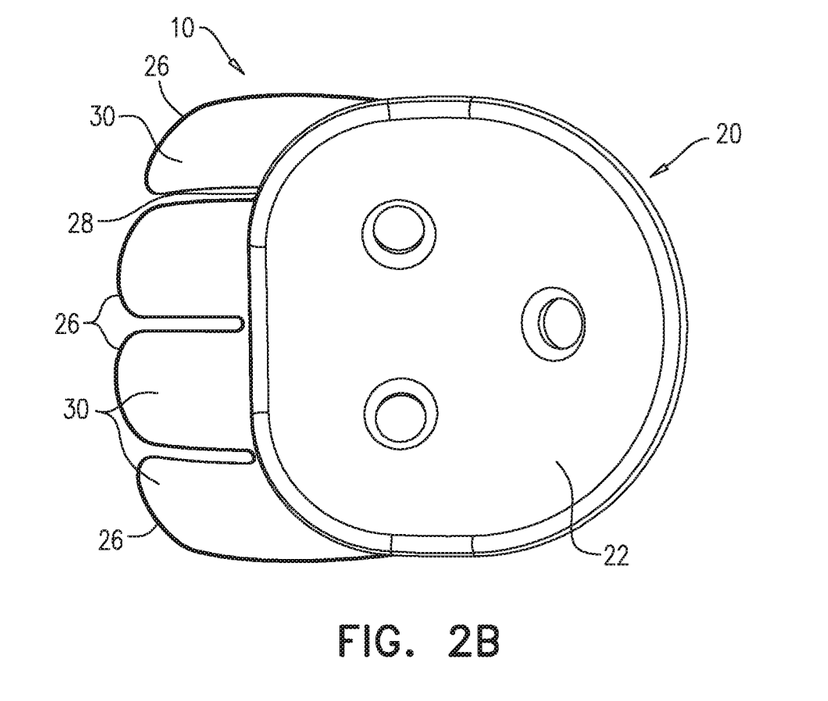

Reference is still made to FIGS. 1A-E, and is additionally made to FIGS. 2A-B, which are schematic illustrations of another configuration of prosthetic glenoid component 10.

For some applications, such as shown in FIGS. 1A-E, bearing body 20 is metallic, and the one or more superior cantilevers 26 are welded to bearing body 20. For some applications, such as shown in FIGS. 1A-E, the two or more superior cantilevers 26 are connected to one another only via bearing body 20. For other applications, such as shown in FIGS. 2A-B, bearing body 20 is polymeric, and the one or more superior cantilevers 26 are inserted into cavities defined in the bearing body and fixated in place with adhesive. For some applications, the two or more superior cantilevers 26 are connected to one another only within 4 mm of periphery 28 of bearing body 20, such as only within 3 mm, e.g., only within 2 mm, of periphery 28 of bearing body 20. Both of these configurations enable the two or more superior cantilevers 26 to flex independently of one another.

Figure 3:
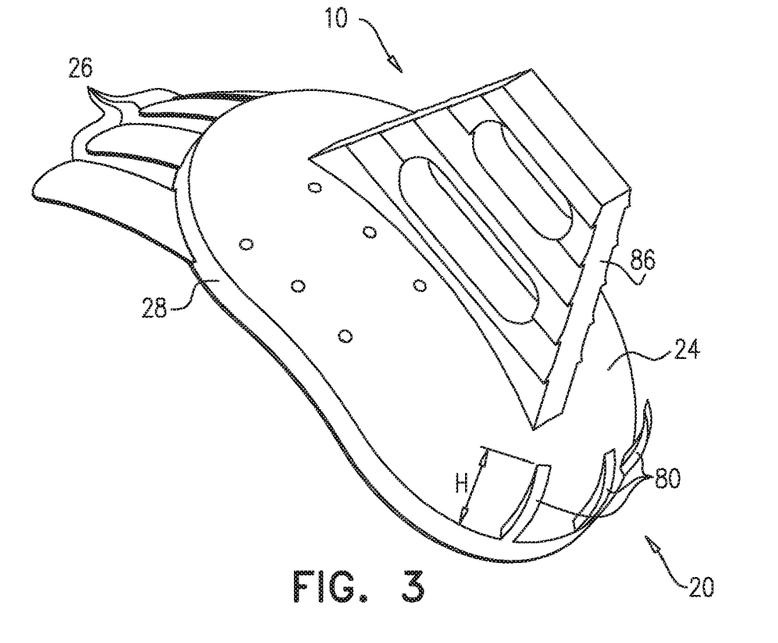
FIG. 3 is a schematic illustration of yet another configuration of the prosthetic glenoid component of FIGS. 1A-E.

Reference is made to FIG. 3, which is a schematic illustration of yet another configuration of prosthetic glenoid component 10. In this configuration, bearing body 20 is shaped so as to define one or more inferior hooks 80, which extend from convex glenoid-contacting surface 24 around a hooked peripheral portion 82 of periphery 28 of bearing body 20 (labeled in FIGS. 1E and 3). (In other words, concave bearing surface 22 is disposed in a first direction from convex glenoid-contacting surface 24, and the one or more inferior hooks 80 extend in a second direction from convex glenoid-contacting surface 24, the second direction opposite the first direction.) The one or more inferior hooks 80 apply a counterforce (typically by friction) against a glenoid cavity 90 (shown in FIGS. 5A-B) to offset the moment of force resulting from the superiorly-directed force applied by superior cantilevers 26. Therefore, hooked peripheral portion 82 is typically disposed on periphery 28 opposite cantilevered peripheral portion 72, described hereinabove with reference to FIG. 1E, and typically does not overlap with cantilevered peripheral portion 72 around periphery 28.

For some applications, hooked peripheral portion 82 is delineated by rays 84 of an angle γ (gamma), which has its vertex 76 at the centroid of periphery 28 of bearing body 20, and is at least 30 degrees, no more than 180 degrees, and/or between 30 and 180 degrees.

Typically, the one or more hooks 80 have an average height H from convex glenoid-contacting surface 24 of at least 2 mm (e.g., at least 5 mm), no more than 20 mm (e.g., no more than 10 mm), and/or between 2 and 20 mm (e.g., between 5 and 10 mm). Typically, hooks 80 include the same material as convex glenoid-contacting surface 24.

For some applications, bearing body 20 is shaped so as to define an anchoring insert 86, which extends from convex glenoid-contacting surface 24. Anchoring insert 86 is configured to be inserted into glenoid cavity 90 (shown in FIGS. 5A-B), and is optionally keel-shaped, as is known in the art. Alternatively, bearing body 20 is not shaped so as to define anchoring insert 86, such as shown in FIGS. 2A-B.

Figure 4:
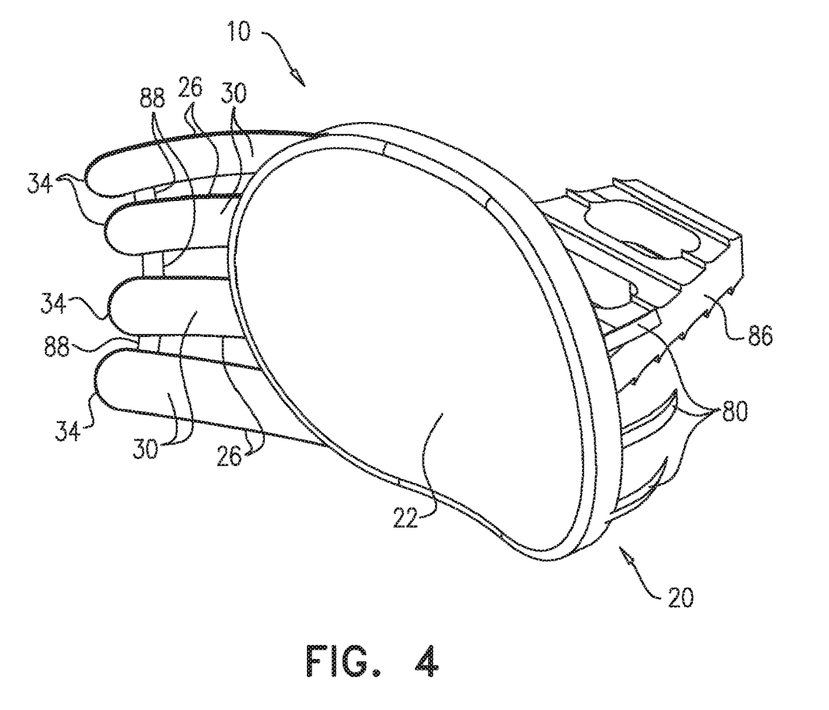
FIG. 4 is a schematic illustration of still another configuration of the prosthetic glenoid component of FIGS. 1A-E.

Reference is made to FIG. 4, which is a schematic illustration of still another configuration of prosthetic glenoid component 10. In this configuration, the two or more superior cantilevers 26 are connected to one another by one or more flexible connecting members 88. Flexible connecting members 88 may be disposed anywhere along superior cantilevers 26, such as, for example, near the respective ends 34, as shown. Flexible connecting members 88 provide mutual support, while still enabling the two or more superior cantilevers 26 to flex independently of one another.

Figure 5A:
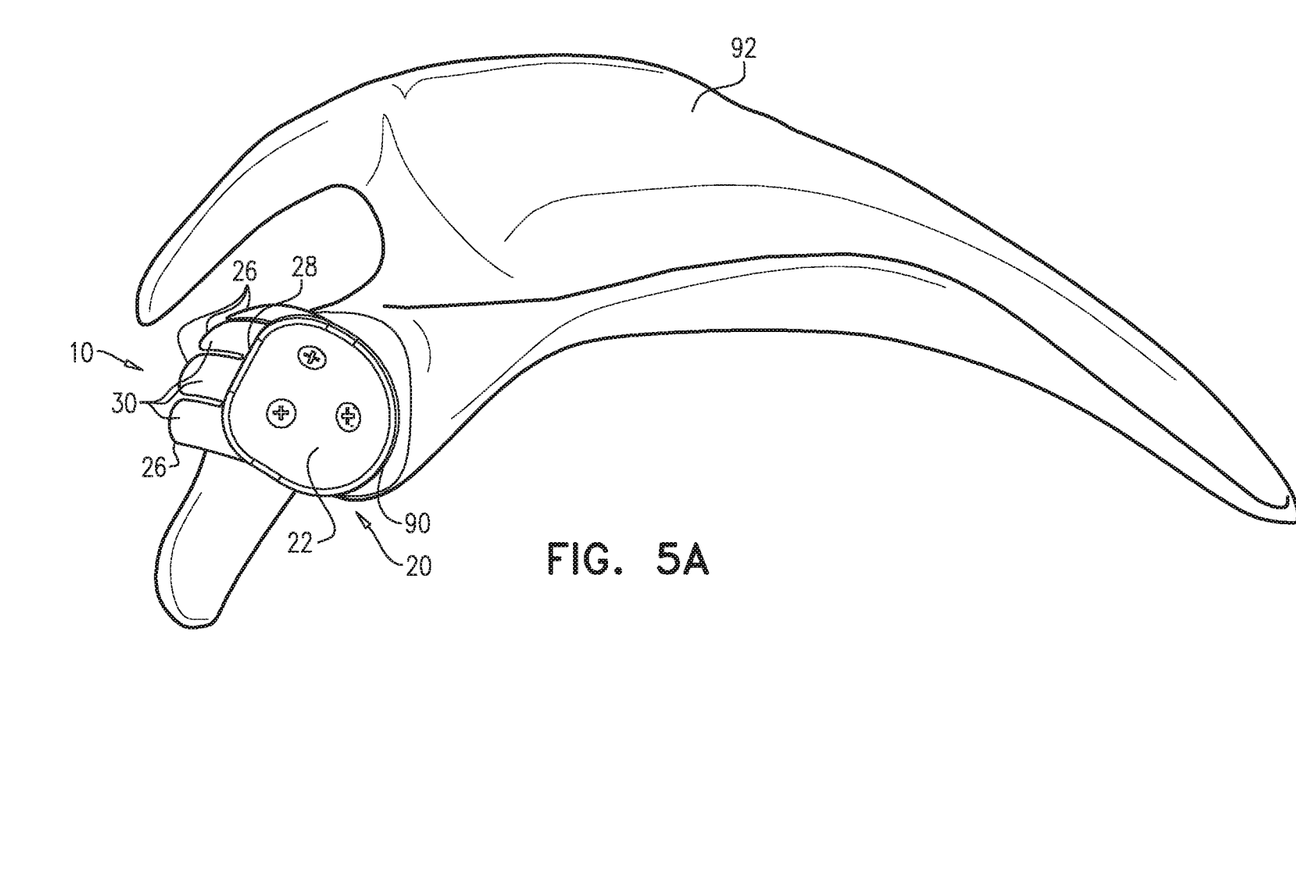
FIGS. 5A-B are schematic illustrations of the prosthetic glenoid component of FIGS. 2A-B implanted in a glenoid cavity of a scapula of a human patient.
Figure 5B:
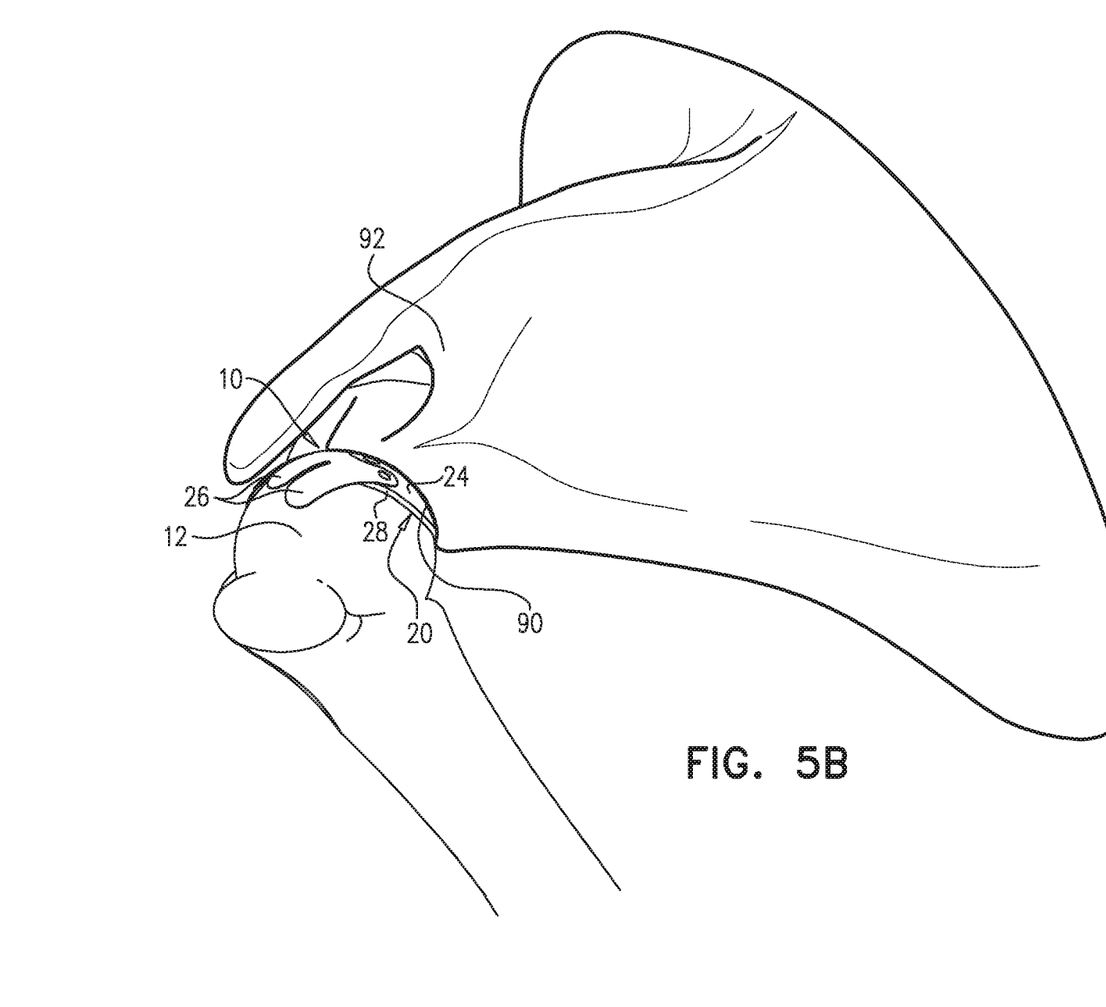

Reference is made to FIGS. 5A-B, which are schematic illustrations of prosthetic glenoid component 10 implanted in glenoid cavity 90 of a scapula 92 of a human patient. As can be seen, prosthetic glenoid component 10 is oriented such that superior cantilevers 26 extend laterally away from glenoid cavity 90, from a superior side of periphery 28 of bearing body 20. Prosthetic glenoid component 10 thus serves to prevent superior migration of (i.e., hold down) humeral head 12, particularly in patients with damaged muscles and/or tendons of the rotator cuff that ordinarily serve this function.

Embodiments of the present invention include features described in the following patents and publications, which are incorporated herein by reference in their entirety. In some embodiments, techniques and apparatus described in one or more of the following patents and publications are combined with techniques and apparatus described herein:

U.S. Pat. No. 8,753,390 to Shohat
U.S. Pat. No. 8,894,713 to Shohat et al.
PCT Publication WO 2008/111073 to Shohat
PCT Publication WO 2010/097724 to Shohat
PCT Publication WO 2012/017438 to Shohat et al.
PCT Publication WO 2013/057566 to Shohat It will be appreciated by persons skilled in the art that the present embodiments are not limited to what has been particularly shown and described hereinabove. Rather, the scope of the present embodiments includes both combinations and subcombinations of the various features described hereinabove, as well as variations and modifications thereof that are not in the prior art, which would occur to persons skilled in the art upon reading the foregoing description.

The invention claimed is:

1. An apparatus comprising a prosthetic glenoid component for use in shoulder arthroplasty for articulation with a humeral head, the prosthetic glenoid component comprising:
   a bearing body, which is shaped so as to define (a) a concave bearing surface for articulation with the humeral head, and (b) a convex glenoid-contacting surface; and
   one or more flexible members, which (a) extend from the bearing body, (b) are more flexible than the bearing body, and (c) resist, without preventing, superior migration of the humeral head.

2. The apparatus according to claim 1, wherein the one or more flexible members are superior cantilevers, each of the superior cantilevers defining a respective convex anterior surface.

3. The apparatus according to claim 2, wherein the one or more flexible members define respective flat anterior surfaces.

4. The apparatus according to claim 1, wherein the one or more flexible members have an average width of between 1 and 8 mm.

5. The apparatus according to claim 1, wherein respective ends of the one or more flexible members farthest from the periphery of the bearing body are rounded.

6. The apparatus according to claim 1, wherein the one or more flexible members define respective anterior surfaces having an aggregate area of between 200 and 1200 mm2.

7. The apparatus according to claim 1,
wherein the one or more flexible members have respective bases, all of which are connected to a cantilevered peripheral portion of a periphery of the bearing body, and
wherein the cantilevered peripheral portion is delineated by the rays of an angle, which has its vertex at the centroid of the periphery of the bearing body, and is no more than 45 degrees.

8. The apparatus according to claim 1, wherein respective ends of the one or more flexible members farthest from a periphery of the bearing body are configured to deflect between 1 and 5 mm upon application of a superiorly-directed force of 1 kN on the one or more flexible members.

9. The apparatus according to claim 1, wherein the prosthetic glenoid component comprises two or more flexible members.

10. The apparatus according to claim 9, wherein the two or more flexible members are shaped and arranged so as to be able to flex independently of one another.

11. The apparatus according to claim 10, wherein the two or more flexible members, when unconstrained, are shaped so as define respective gaps between adjacent ones of the two or more flexible members.

12. The apparatus according to claim 11, wherein each of the gaps has average width of between 0.1 and 2 mm.

13. The apparatus according to claim 11, wherein each of the gaps has average width of between 2.5% and 100% of an average width of the two or more flexible members.

14. The apparatus according to claim 10, wherein the two or more flexible members are connected to one another only within 4 mm of the periphery of the bearing body.

15. The apparatus according to claim 10, wherein the two or more flexible members are connected to one another only via the bearing body.

16. The apparatus according to claim 10, wherein the two or more flexible members are connected to one another by one or more flexible connecting members.

17. The apparatus according to claim 1, wherein the bearing body is shaped so as to define one or more inferior hooks, which extend from the convex glenoid-contacting surface around a hooked peripheral portion of the periphery of the bearing body.

18. The apparatus according to claim 17,
wherein the one or more flexible members have respective bases, all of which are connected to a cantilevered peripheral portion of the periphery of the bearing body, and
wherein the hooked peripheral portion is disposed on the periphery opposite the cantilevered peripheral portion.

19. A method comprising:
providing a prosthetic glenoid component for use in shoulder arthroplasty for articulation with a humeral head, the prosthetic glenoid component comprising (a) a bearing body, which is shaped so as to define (i) a concave bearing surface for articulation with the humeral head, and (ii) a convex glenoid-contacting surface, and (b) one or more flexible members, which (i) extend from the bearing body; and
as part of the shoulder arthroplasty, implanting the prosthetic glenoid component such that the convex glenoid-contacting surface contacts a glenoid cavity, and the one or more flexible members resist, without preventing, superior migration of the humeral head.

* * * * *